United States Patent
Becker et al.

(10) Patent No.: US 6,176,828 B1
(45) Date of Patent: Jan. 23, 2001

(54) METHOD AND APPARATUS FOR OPTIMAL DATA MAPPING OF POWER DOPPLER IMAGES

(75) Inventors: David D. Becker, Milwaukee, WI (US); Mir Said Seyed-Bolorforosh, Palo Alto, CA (US); Michael Joseph Washburn, New Berlin, WI (US)

(73) Assignee: General Electric Company, Milwaukee, WI (US)

( * ) Notice: Under 35 U.S.C. 154(b), the term of this patent shall be extended for 0 days.

(21) Appl. No.: 09/220,519

(22) Filed: Dec. 24, 1998

(51) Int. Cl.[7] ............................................. A61B 8/00
(52) U.S. Cl. ........................................................ 600/440
(58) Field of Search ................................. 600/437, 440, 600/445, 446

(56) References Cited

U.S. PATENT DOCUMENTS 5,471,990  * 12/1995  Thirsk ..................................... 600/445
5,882,306  *  3/1999  Ramamurthy et al. ............... 600/440
5,961,460  * 10/1999  Guracar et al. ....................... 600/440

* cited by examiner

*Primary Examiner*—Marvin M. Lateef
*Assistant Examiner*—Maulin Patel
(74) *Attorney, Agent, or Firm*—Dennis M. Flaherty; Christian G. Cabou; Phyllis Y. Price

(57) ABSTRACT

A method and an apparatus for color mapping of flow power data in which the flow states containing information of most interest to the user are enhanced, while flow states not containing information of interest are suppressed. This is accomplished using a color mapping having three segments which are connected at upper and lower knee points, the latter being settable either automatically or via operator inputs. In the automatic mode, the host computer determines the positions of the knee points based on analysis of a single or a mean image frame of power Doppler data or based on system parameters (e.g., dynamic range) set by the operator. The host computer then constructs a color mapping having the determined knee points and loads that color mapping into the video processor.

23 Claims, 2 Drawing Sheets

METHOD AND APPARATUS FOR OPTIMAL DATA MAPPING OF POWER DOPPLER IMAGES

FIELD OF THE INVENTION

This invention generally relates to ultrasound power Doppler imaging of fluid flow fields. In particular, the invention relates to methods and apparatus for imaging blood flowing in the human body by detecting the power in the ultrasonic echoes reflected from the flowing blood.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase, shift translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, the color flow mode displays hundreds of adjacent sample volumes simultaneously, all laid over a B-mode image and color-coded to represent each sample volume's velocity. The power Doppler mode also displays sample volumes laid over a B-mode image, but the displayed sample volumes are color-coded to represent the power or energy of the signals reflected from each sample volume.

In standard color flow processing, a high pass filter known as a wall filter is applied to the data before a color flow estimate is made. The purpose of this filter is to remove signal components produced by tissue surrounding the blood flow of interest. If these signal components are not removed, the resulting velocity or power estimate will be a combination of the velocity or power of the signal returned from the blood flow and the velocity or power of the signal returned from the surrounding tissue. The backscatter component from tissue is many times larger than that from blood, so the parameter estimate will most likely be more representative of the tissue, rather than the blood flow. In order to get the flow velocity or power, the tissue signal must be filtered out.

In the color flow mode of a conventional ultrasound imaging system, an ultrasound transducer array is activated to transmit a series of multi-cycle (typically 4–8 cycles) tone bursts which are focused at the same transmit focal position with the same transmit characteristics. These tone bursts are fired at a pulse repetition frequency (PRF). The PRF is typically in the kilohertz range. A series of transmit firings focused at the same transmit focal position are referred to as a "packet". Each transmit beam propagates through the object being scanned and is reflected by ultrasound scatterers such as blood cells. The returned signals are detected by the elements of the transducer array and then formed into a receive beam by a beamformer.

For example, the traditional color firing sequence is a series of firings (e.g., tone bursts) along the same position, which firings produce the respective receive signals:

$$F_1\ F_2\ F_3\ F_4\ \ldots\ F_M$$

where $F_i$ is the receive signal for the i-th firing and M is the number of firings in a packet. These receive signals are loaded into a corner turner memory, and a high pass filter (wall filter) is applied to each down range position across firings, i.e., in "slow time". In the simplest case of a (1, −1) wall filter, each range point will be filtered to produce the respective difference signals:

$$(F_1-F_2)(F_2-F_3)(F_3-F_4)\ldots(F_{M-1}-F_M)$$

and these differences are input to a color flow power estimator.

Power Doppler imaging maps the power or energy in blood flow over a two-dimensional image. The transfer function of the resultant displayed power Doppler image is the product of the transfer function of the underlying compression curve and a mapping function. State-of-the-art ultrasound systems typically give the user a series of mapping functions from which to choose. These mapping functions provide for an arbitrary selection of displayed colors, but do not allow the user or the system to optimize the image information based either on user settings or imaging data itself.

SUMMARY OF THE INVENTION

The present invention is a method and an apparatus for color mapping of flow power data in which the flow states containing information of most interest to the user are enhanced while flow states not containing information of interest are suppressed. This is accomplished using a color mapping having an optimal form. In accordance with that optimal form, the color mapping function comprises three segments which are connected at upper and lower knee points, which are settable either automatically or via operator inputs. The color intensity values of the first, second and third mapping segments are applied to the power Doppler imaging data in low, middle and high ranges respectively. The lower knee point is positioned based on the system noise floor of the power Doppler imaging data and the upper knee point is positioned x units higher than the lower knee point along the power Doppler imaging data axis of the mapping function, where x is defined as the useful flow dynamic range and signal-to-noise ratio.

In accordance with one preferred embodiment, the upper and lower knee points can be adaptively determined from the power Doppler imaging data available. In particular, this function can be performed automatically by the host computer. For example, the host computer can perform an image analysis algorithm on one or more frames of power Doppler imaging data retrieved from cine memory, determine the optimal location of the upper and lower knee points based on the analyzed power Doppler imaging data, construct an optimal color mapping function having the optimally located knee points, and then load the optimal color mapping function into the video processor. In particular, the positions of the knee points can be determined as a function of the signal-to-noise ratio or the dynamic range, which can be estimated from the power Doppler imaging data during image analysis.

Alternatively, the host computer can be programmed to adaptively determine the positions of the knee points of the color mapping function based on user-selected inputs, e.g., the system color flow gain setting or the dynamic range setting.

In accordance with a further preferred embodiment, the position(s) of one or both knee points of the color mapping function can be moved by the user through the operator interface. In one mode, the user can move the positions of the upper and lower knee points in tandem. This will allow the user to shift the entire curve up or down to trade off between display states used for low versus high flow states. In another mode, the user can move position of the lower knee point relative to the position of the upper knee point. This change in the position of the lower knee point changes the slope of the curve in the useful flow dynamic range area (x) and the effective dynamic range in the display space. In response to operator inputs changing the position(s) of one or both knee points, the host computer constructs a color mapping function having the knee point positions requested by the user and loads that color mapping into the video processor.

DETAILED DESCRIPTION OF THE PREFERRED EMBODIMENTS

Figure 1:
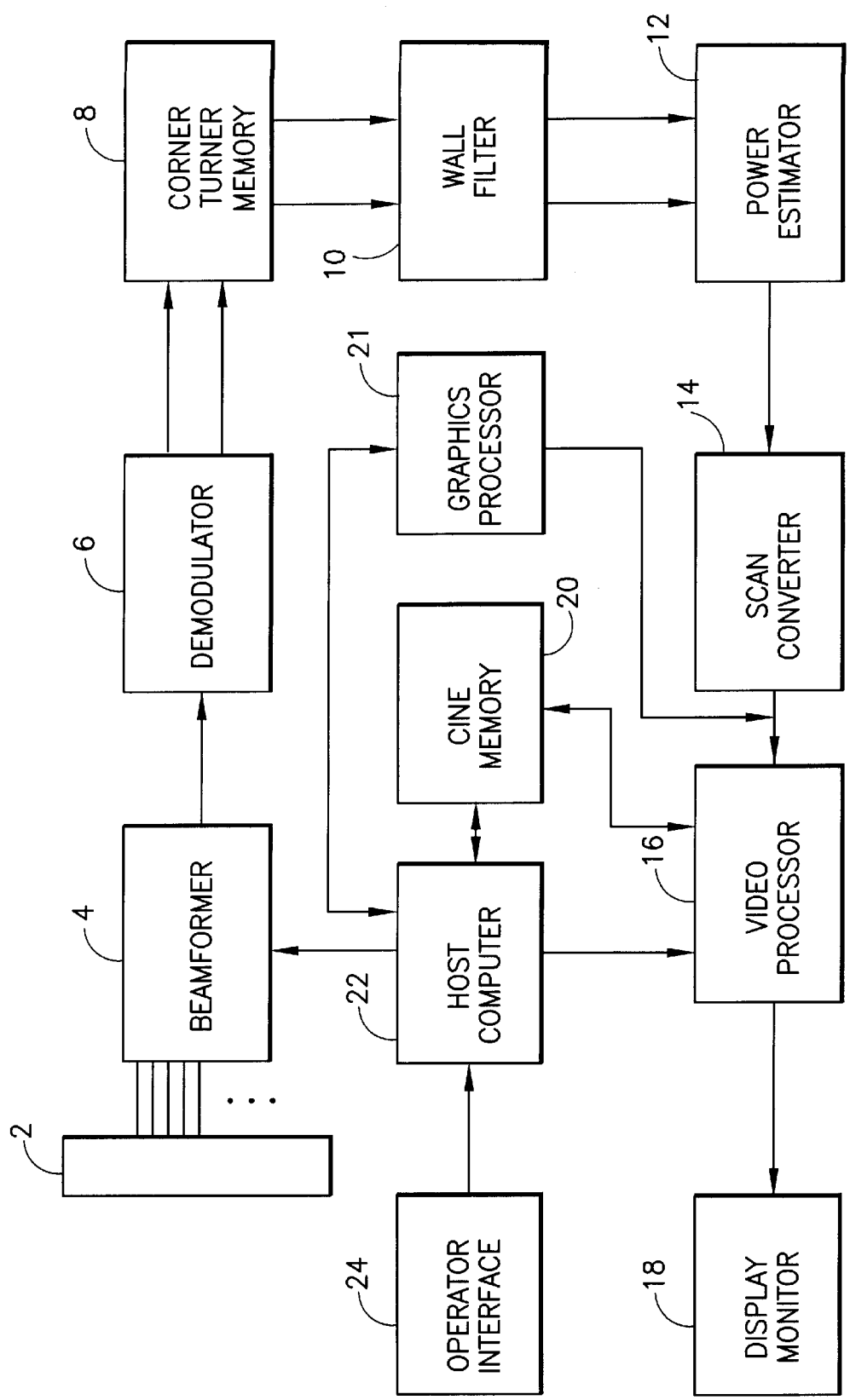
FIG. 1 is a block diagram showing the signal processing chain for a color flow ultrasound imaging system programmed to incorporate the present invention.

Referring to FIG. 1, the basic signal processing chain for a color flow imaging system comprises an ultrasound transducer array 2, which is activated to transmit pulse sequences comprising tone bursts of length P which are fired repeatedly at the PRF. The return RF signals are detected by the transducer elements and received by the respective receive channels in the beamformer 4. The beamformer sums the delayed channel data and outputs a beamsummed signal, which is demodulated into in-phase and quadrature (I/Q) signal components by a demodulator 6. The I/Q signal components are stored in a corner turner memory 8, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through respective wall filters 10, which reject any clutter corresponding to stationary or very slow-moving tissue. The filtered outputs are then fed into a power estimator 12, which converts the range cell information into the intermediate autocorrelation parameter R(0). R(0) is approximated as a finite sum over the number of firings in a packet, as follows:

$$R(0) = \sum_{i=1}^{M-1} \frac{(I_i^2 + Q_i^2 + I_{i+1}^2 + Q_{i+1}^2)}{2}$$

where $I_i$ and $Q_i$ are the demodulated, basebanded input data for firing i, and M is the number of firings in the packet. The signal R(0), which represents the amount of the returned power in the Doppler-shifted flow signal, indicates the strength of the signal from the flowing reflectors.

The power Doppler estimates R(0) are sent to a scan converter 14, which converts the power Doppler imaging data into X-Y format. The scan-converted frames are passed to a video processor 16, which basically maps the power Doppler imaging data in accordance with one or more color mapping functions for video display. The image frames of power Doppler imaging data are then sent to the video monitor 18 for display.

The power Doppler images displayed by monitor 18 are produced from an image frame of data in which each datum indicates the intensity or brightness of a respective pixel in the display. An image frame may, e.g., comprise a 256×256 data array in which each display intensity datum is an 8-bit binary number that indicates pixel brightness. Each pixel has an intensity value which is a function of the power or energy of the echo signals returned from a corresponding range gate in the blood flow in response to interrogating ultrasonic pulses and the color mapping employed. The displayed power Doppler image represents the blood flow in a plane through the body being imaged.

In the system shown in FIG. 1, successive frames of power Doppler data are stored in a cine memory 20 on a first-in, first-out basis. The cine memory 20 stores the power Doppler data which has already been converted in the first portion of the video processor to the video frame rate, but before color mapping. Storage can be continuous or as a result of an external trigger event. The cine memory 20 is like a circular image buffer that runs in the background, capturing imaging data that is displayed in real time to the user. When the user freezes the system (by operation of an appropriate device on the operator interface 24), the user has the capability to view power Doppler imaging data previously captured in cine memory.

System control is centered in a host computer 22, which accepts operator inputs through the operator interface 24 (e.g., a control panel) and in turn controls the various subsystems. In particular, the host computer provides transmit time delays, amplitude control and transmit sequences to the transmitter of beamformer 4, and provides receive time delays to the receiver of the beamformer, either directly or via a scan controller (not shown).

The conventional system has the capability to superimpose graphical symbols on any ultrasound image. The superimposition of graphics on the image frame is accomplished in the video processor 16, which receives the ultrasound image frame from an X-Y display memory in the scan converter 14 and the graphics data from a graphics display memory (not shown). The graphics data is processed and input into the graphics display memory by a graphics processor 21 which is synchronized with the other subsystems by the host computer.

Figure 2:
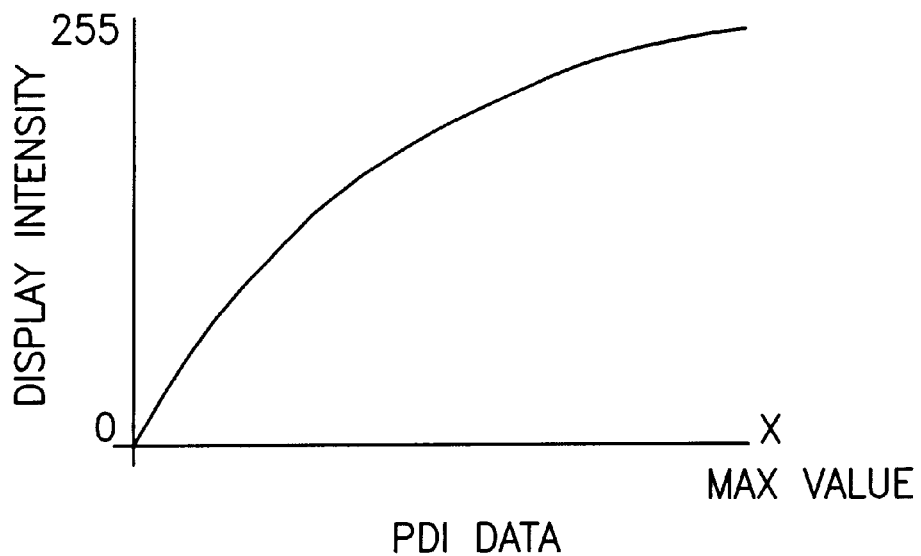
FIG. 2 is a graph showing an arbitrary color mapping function for power Doppler imaging.

As previously disclosed, the color mapping function is carried out by the video processor, the latter in turn being programmable by the host computer. An arbitrary color mapping function, for mapping flow power or energy to displayed color and intensity, is shown in FIG. 2, with the power Doppler imaging data values increasing from left to right along the horizontal axis and the display color intensity values increasing from bottom to top along the vertical axis. For color display data, a separate curve can be shown for each of the colors red, green and blue, or any three arbitrary colors which span the system's display space. The respective curves for the three colors are designed to emphasize a respective one of the colors in a respective range of power Doppler imaging data values.

An optimal image results from defining a mapping which displays all available imaging data, while enhancing the flow states which contain the information of most interest to the user and suppressing flow states that do not contain pertinent information. Because the color mapping function shown in FIG. 2 compresses the middle range of power Doppler imaging data values more than it compresses the lower range, the mapping of FIG. 2 is not optimal for power Doppler imaging data in which the mid-level flow states are of greatest interest.

Figure 3:
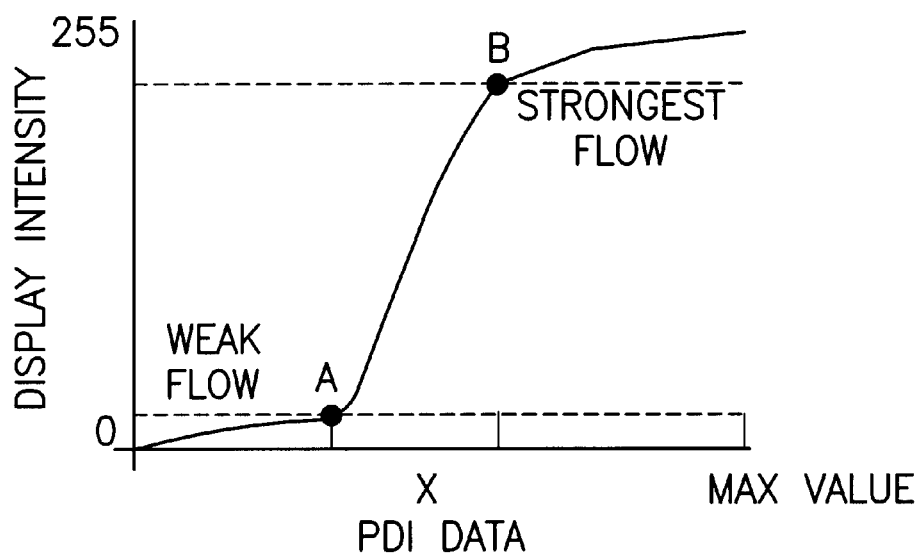
FIG. 3 is a graph showing a generalized optimal color mapping function for power Doppler imaging in accordance with one preferred embodiment of the invention.

The present invention is a method and an apparatus for color mapping of flow power data in which the flow states containing information of most interest to the user are enhanced while flow states not containing information of interest are suppressed. This is accomplished using a color mapping having the generalized optimal form shown in FIG. 3. In accordance with that optimal form, the color mapping function comprises three segments 26, 28 and 30, which are connected at lower and upper knee points A and B. The color intensity values of the first, second and third mapping segments are applied to the power Doppler imaging data in low, middle and high ranges respectively, the first and second mapping segments 26 and 28 being connected at the lower knee point A and the second and third mapping segments 28 and 30 being connected at the upper knee point B. Point A is preferably set just above the system noise floor. Low flow intensities to the left of point A represent noise mixed with the lowest detectable signals, and are compressed, or allotted very little of the display space on the vertical axis. Point B represents the point above which the strongest flow states are compressed and also allotted little of the vertical axis display space. Flow states in between points A and B are of greatest interest, and are allotted the greatest number of output display states, i.e., the power Doppler data for these flow states is expanded, not compressed. The optimal mapping function will preferably assign point A based on the system noise floor and point B to be x units above point A, where x is defined as the useful flow dynamic range and signal to noise ratio.

In accordance with another preferred embodiment, the upper and lower knee points can be adaptively determined from the power Doppler imaging data available and then a color mapping can be constructed based on the determined knee points. These functions can be performed automatically by the host computer. The automatic color mapping construction can be activated via a single button (or soft-key) incorporated in the operator interface. In response to activation, the image is frozen momentarily to allow one to several most recent image frames to be saved to cine memory, which can then be read out by the host computer for analysis. If more than one is used, a mean is taken to reduce statistical variations before image analysis. In particular, the positions of the knee points can be determined as a function of the signal-to-noise ratio (for each power Doppler imaging datum) or the dynamic range (by organizing the power Doppler imaging datum into a histogram), which can be estimated from the power Doppler imaging data during image analysis. The host computer can perform an image analysis algorithm on a single image frame of power Doppler data retrieved from cine memory or on a mean image frame formed by retrieving multiple image frames from cine memory and calculating the mean for each pixel to form a mean image frame. The host computer then determines the optimal location of the upper and lower knee points based on the analyzed power Doppler imaging data, constructs an optimal color mapping function having the optimally located knee points, and loads the optimal color mapping function into the video processor.

Alternatively, the host computer can be programmed to adaptively determine the positions of the knee points of the color mapping function based on user-selected inputs, e.g., the system color flow gain setting or the dynamic range setting, and then construct a color mapping having knee points at those positions.

The automated color mapping construction can be implemented in software by the host computer. In the most geometrically simple case, the three mapping segments 26, 28 and 30 in FIG. 3 can be linear segments. Upon determination of the knee point positions based on either operator settings or analyzed image data, the mapping of power Doppler values into display intensity values can be readily calculated for each linear mapping segment. In accordance with the preferred embodiments of the invention, the slope of mapping segment 28 is greater than the slope of mapping segment 26 and greater than the slope of mapping segment 30.

It will be readily appreciated that the mapping segments may be curvilinear. In that event, the slope of a line connecting the knee points A and B will be greater than the slope of a line connecting knee point A with the start point of the mapping curve and greater than the slope of a line connecting knee point B with the end point of the mapping curve.

In accordance with a further preferred embodiment, the position(s) of one or both knee points of the color mapping function can be moved by the user through the operator interface. In response to activation of a single button (or soft-key) incorporated in the operator interface, the host computer 22 (see FIG. 1) sends the current color mapping function to the graphics processor 21 for display on the display monitor 18. Using a trackball, mouse or other input device, the operator may superimpose a graphical symbol on a knee joint of the displayed color mapping function and then operate the input device to move that symbol to the desired position. In one mode, the user can move the positions of the upper and lower knee points in tandem. This will allow the user to shift the entire curve up or down to trade off between display states used for low versus high flow states. If desired, the knee points can also be moved leftward or rightward in tandem. In another mode, the user can move position of the lower knee point relative to the position of the upper knee point. This change in the position of the lower knee point changes the slope of the curve in the useful flow dynamic range area (x) and the effective dynamic range in the display space. In response to operator inputs changing the position(s) of one or both knee points, the host computer constructs a color mapping function having the knee point positions requested by the user and loads that color mapping into the video processor.

The lower and upper knee points A and B can be optimally determined from the imaging data available. This can be demonstrated in a renal scan, where the optimal mapping will display the slowest flow at the edges of the kidney at the just detectable level of point A while mapping strong flow levels of the renal artery at point B so that they do not saturate the image, and allowing the greatest display dynamic range between points A and B for mid-level flow states.

The foregoing preferred embodiments have been disclosed for the purpose of illustration. Variations and modifications of the concept of the invention will be readily apparent to persons skilled in the art. All such variations and modifications are intended to be encompassed by the claims set forth hereinafter.

As used in the claims, the phrase "as a function of" is not to be construed to mean "as a function of only" what follows. For example, in accordance with the foregoing definition, the phrase "determine y as a function of x" would read on all cases where y was determined as a function of x alone or as a function of x and one or more other variables, e.g., z.

What is claimed is:

1. A system for imaging biological tissues, comprising:
   an ultrasound transducer array comprising a multiplicity of transducer elements;
   a transmit beamformer for pulsing said transducer array to transmit ultrasound beams in a scan plane;
   a receive beamformer for forming receive beams of acoustic data derived from echo signals detected by the transducer array subsequent to said transmissions;
   a signal processing chain for converting said acoustic data into an image frame of power Doppler imaging data;
   a video processor for color mapping said power Doppler imaging data in accordance with a current color mapping function having upper and lower knee points;
   an operator interface for selecting a change in the position of at least one of said upper and lower knee points;
   a computer programmed to construct a new color mapping function as a function of said selected change in position and load said new color mapping function into said video processor; and
   a display device for displaying an image representing a color-mapped image frame of power Doppler imaging data.

2. The system as recited in claim 1, wherein a slope of a line connecting said knee points of said new color mapping function is greater than a slope of a line connecting said lower knee point and a start point of said new color mapping function and greater than a slope of a line connecting said upper knee point and an end point of said new color mapping function.

3. The system as recited in claim 1, wherein a said computer is further programmed to move said lower and upper knee points in tandem in response to said selection via said operator interface.

4. A system for imaging biological tissues, comprising:
   an ultrasound transducer array comprising a multiplicity of transducer elements;
   a transmit beamformer for pulsing said transducer array to transmit ultrasound beams in successive scans;
   a receive beamformer for forming receive beams of acoustic data derived from echo signals detected by the transducer array subsequent to said transmissions;
   a signal processing chain for converting said acoustic data into successive image frames of power Doppler imaging data;
   memory for storing said power Doppler imaging data;
   a video processor for color mapping image frames of power Doppler imaging data in accordance with a current color mapping function;
   a display device for displaying successive image respectively representing successive color-mapped image frames of power Doppler imaging data; and
   a computer programmed to perform the followings steps:
   (a) retrieving at least one image frame of power Doppler imaging data from said memory;
   (b) analyzing said retrieved power Doppler imaging data;
   (c) determining the positions of lower and upper knee points as a function of the results of said analyzing step;
   (d) constructing a new color mapping function having lower and upper knee points at said determined positions; and
   (e) loading said new color mapping function into said video processor.

5. The system as recited in claim 4, wherein a slope of a line connecting said knee points of said new color mapping function is greater than a slope of a line connecting said lower knee point and a start point of said new color mapping function and greater than a slope of a line connecting said upper knee point and an end point of said new color mapping function.

6. The system as recited in claim 4, wherein said analyzing step comprises the step of determining a signal-to-noise ratio for each power Doppler imaging datum in a retrieved image frame.

7. The system as recited in claim 4, wherein said analyzing step comprises the step of determining a mean signal-to-noise ratio for each set of power Doppler imaging datum corresponding to a respective pixel in multiple retrieved image frames.

8. The system as recited in claim 4, wherein said analyzing step comprises the step of determining the dynamic range of said power Doppler imaging data in one or more retrieved image frames.

9. A system for imaging biological tissues, comprising:
   an ultrasound transducer array comprising a multiplicity of transducer elements;
   a transmit beamformer for pulsing said transducer array to transmit ultrasound beams in a scan plane;
   a receive beamformer for forming receive beams of acoustic data derived from echo signals detected by the transducer array subsequent to said transmissions;
   a signal processing chain for converting said acoustic data into an image frame of power Doppler imaging data;
   a video processor for color mapping said power Doppler imaging data in accordance with a current color mapping function;
   an operator interface for setting a system parameter;
   a display device for displaying an image representing a color-mapped image frame of power Doppler imaging data; and
   a computer programmed to perform the followings steps:
   (a) retrieving said system parameter setting;
   (b) determining the positions of lower and upper knee points as a function of said system parameter setting;
   (c) constructing a new color mapping function having lower and upper knee points at said determined positions; and
   (d) loading said color mapping function into said video processor.

10. The system as recited in claim 9, wherein a slope of a line connecting said knee points of said color mapping function is greater than a slope of a line connecting said lower knee point and a start point of new color mapping function and greater than a slope of a line connecting said upper knee point and an end point of said color mapping function.

11. The system as recited in claim 9, wherein said system parameter is system color flow gain.

12. The system as recited in claim 9, wherein said system parameter is dynamic range.

13. A system for imaging biological tissues, comprising:
   an ultrasound transducer array comprising a multiplicity of transducer elements;
   a transmit beamformer for pulsing said transducer array to transmit ultrasound beams in a scan plane;
   a receive beamformer for forming receive beams of acoustic data derived from echo signals detected by the transducer array subsequent to said transmissions;

a signal processing chain for converting said acoustic data into an image frame of power Doppler imaging data;

a video processor for color mapping said power Doppler imaging data in accordance with a current color mapping function having upper and lower knee points;

a display device for displaying an image representing said current color mapping function;

an operator interface for moving a graphical symbol superimposed on said displayed image to select a change in the position of at least one of said upper and lower knee points of said current color mapping function; and a computer programmed to construct a new color mapping function as a function of said selected change in position and load said new color mapping function into said video processor.

14. The system as recited in claim 13, wherein a said computer is further programmed to move said lower and upper knee points in tandem in response to said selection via said operator interface.

15. A method for programming an ultrasound imaging system, comprising the steps of:

acquiring successive image frames of power Doppler imaging data;

storing a current color flow mapping function;

color mapping said successive image frames of power Doppler imaging data in accordance with said current color mapping function;

analyzing at least one image frame of power Doppler imaging data;

determining the positions of lower and upper knee points as a function of the results of said analyzing step;

constructing a new color mapping function having lower and upper knee points at said determined positions; and storing said new color mapping function in place of said current color mapping function.

16. The method as recited in claim 15, wherein a slope of a line connecting said knee points of said new color mapping function is greater than a slope of a line connecting said lower knee point and a start point of said new color mapping function and greater than a slope of a line connecting said upper knee point and an end point of said new color mapping function.

17. The method as recited in claim 15, wherein said analyzing step comprises the step of determining a signal-to-noise ratio for each power Doppler imaging datum in a retrieved image frame.

18. The method as recited in claim 15, wherein said analyzing step comprises the step of determining a mean signal-to-noise ratio for each set of power Doppler imaging datum corresponding to a respective pixel in multiple retrieved image frames.

19. The method as recited in claim 15, wherein said analyzing step comprises the step of determining the dynamic range of said power Doppler imaging data in one or more retrieved image frames.

20. A method for operating an ultrasound imaging system, comprising the steps of:

acquiring a first image frame of power Doppler imaging data;

color mapping said first image frame of power Doppler imaging data in accordance with a current color mapping function;

displaying a first image representing said color-mapped first image frame of power Doppler imaging data;

freezing said system after said first image frame has been displayed;

while said system is frozen, performing the following steps: analyzing said first image frame of power Doppler imaging data; determining the positions of lower and upper knee points as a function of the results of said analyzing step; constructing a new color mapping function having lower and upper knee points at said determined positions; and substituting said new color mapping function in place of said current color mapping function;

unfreezing said system after said step of substituting;

acquiring a second image frame of power Doppler imaging data;

color mapping said second image frame of power Doppler imaging data in accordance with said new color mapping function; and displaying a second image representing said color-mapped second image frame of power Doppler imaging data.

21. A method for programming a video processor of an ultrasound imaging system with a color mapping function, comprising the steps of:

retrieving a system parameter setting;

determining the positions of lower and upper knee points as a function of said system parameter setting;

constructing a color mapping function having lower and upper knee points at said determined positions; and loading said color mapping function into said video processor.

22. The method as recited in claim 21, wherein a slope of a line connecting said knee points of said color mapping function is greater than a slope of a line connecting said lower knee point and a start point of said color mapping function and greater than a slope of a line connecting said upper knee point and an end point of said color mapping function.

23. A system for imaging biological tissues, comprising:

means for acquiring successive image frames of power Doppler imaging data;

memory for storing said image frames of power Doppler imaging data;

means for color mapping said image frames of power Doppler imaging data in accordance with a current color mapping function;

means for displaying respective images representing said color-mapped image frames of power Doppler imaging data;

means for retrieving at least one image frame of power Doppler imaging data from said memory;

mean for analyzing said retrieved power Doppler imaging data;

means for determining the positions of lower and upper knee points as a function of the output of said analyzing means;

means for constructing a new color mapping function having lower and upper knee points at said determined positions; and means for loading said new color mapping function into said color mapping means.

* * * * *